United States Patent [19]

Polyak

[11] Patent Number: 5,254,092
[45] Date of Patent: Oct. 19, 1993

[54] FLUID FLOW CHECK VALVE

[75] Inventor: Mark Polyak, Minnetonka, Minn.

[73] Assignee: American Medical Systems, Inc., Minnetonka, Minn.

[21] Appl. No.: 945,056

[22] Filed: Sep. 15, 1992

[51] Int. Cl.⁵ .............. A61M 29/00; A61M 5/00; F16K 15/18; F16K 15/00
[52] U.S. Cl. ........................ 604/99; 604/97; 604/247; 604/250; 137/512; 137/523
[58] Field of Search ................. 604/8-10, 604/96, 97-99, 246, 247, 250, 256; 137/512, 522, 523

[56] References Cited

U.S. PATENT DOCUMENTS

| | | | |
|---|---|---|---|
| 543,773 | 7/1895 | Massey | 137/523 |
| 2,314,767 | 3/1943 | Burrell | 604/250 X |
| 3,547,147 | 12/1970 | Shay | 137/522 |
| 3,701,478 | 10/1972 | Tada . | |
| 3,985,140 | 10/1976 | Harris | 604/9 |
| 4,390,188 | 6/1983 | Rouse | 280/6.1 |
| 4,580,596 | 4/1986 | Stehling | 137/523 |
| 4,588,394 | 5/1986 | Schulte et al. | 604/9 |
| 4,605,200 | 8/1986 | Huppee | 251/258 |
| 4,662,871 | 5/1987 | Rafelson | 604/119 |
| 4,940,459 | 7/1990 | Noce . | |
| 5,015,233 | 5/1991 | McGough et al. . | |

*Primary Examiner*—John D. Yasko
*Assistant Examiner*—Adam J. Cermak
*Attorney, Agent, or Firm*—Peter C. Richardson; Lawrence C. Akers; Mark Dryer

[57] ABSTRACT

A valve for controlling the flow of fluid through a flow path, which valve comprises a housing defining a flow path and having two indented portions about the flow path, a poppet mounted within each indented portion such that the internal end of each indented portion defines a seat which provides a fluid tight seal when the associated poppet head is held against the seat, a spring associated with each poppet for holding each poppet against each seat, a rigid moveable member associated with each poppet and adapted to alter the orientation of the associated poppet relative to its seat and thereby seal or unseal the flow path around the poppet, and an actuator for moving each movable member; and inflator apparatus incorporating at least one valve.

13 Claims, 8 Drawing Sheets

FLUID FLOW CHECK VALVE

BACKGROUND OF INVENTION

This invention relates to a valve for controlling flow of a fluid through a flow path and particularly to a check valve for use with medical apparatus such as an inflatable catheter. More particularly, the invention is concerned with a four-way check valve for controlling the flow of liquid in a medical apparatus such as an inflator for a balloon catheter or a pump for an implantable inflatable prosthesis.

U.S. Pat. No. 3,701,478 discloses a hand sprayer which consists of a hand-operated piston-type pump and includes a check valve which is adapted to open upon the application of pressure.

U.S. Pat. Nos. 4,940,459 and 5,015,233 disclose inflation devices for inflating balloon catheters involving trigger-operated plungers.

It has now been found that inflation devices, particularly inflators for balloon dilation catheters and pumps for inflatable penile prostheses may be improved and made more convenient for the user, for example by facilitating operation with a single hand and preventing over pressurization, if the apparatus includes a unique valve as described hereinafter.

SUMMARY OF INVENTION

In accordance with the present invention there is provided an element of a valve for controlling flow of a fluid through a flow path, which element comprises a housing defining said flow path and having an indented portion about said flow path, a poppet mounted within said indented portion such that an internal end of the indented portion defines a seat which provides a fluid-tight seal when the poppet mounted within the indented portion is held against said seat, spring means for holding said poppet against said seat, a rigid movable means associated with the poppet for altering the orientation of said poppet relative to said seat and thereby seal or unseal the flow path, and actuating means for moving said movable means.

Preferably, the wall of the indented portion on the opposite side of the wall adjacent to and actuated by the movable member, i.e. the distal wall, has a stepped profile, as shown in the embodiments illustrated in the accompanying drawings, to provide a step about which the poppet can pivot when it is moved by the movable member. This pivotal action facilitates opening of the valve element.

As used herein the term "valve" is intended to mean a device which controls the flow of a fluid in a flow path either by sealing the path so that flow is prevented, herein defined as the "check" position; or by allowing flow in a given direction, herein defined as the "pass" position.

The term "element of a valve" or "valve element" refers to a part of a valve which has sufficient members to perform the "check" and "pass" (unidirectional) functions as will be more particularly described hereinafter. A "valve" according to the invention comprises at least two "elements".

The term "poppet" means a spring-loaded member preferably having a generally cup-shaped profile with a flat forward "head" and being adapted to be held, by spring means positioned within the cup, against a "seat" to form a seal whereby flow is prevented in the back-to-front direction of the poppet, herein defined as the "check" position. Flow in the front-to-back direction may be possible if the fluid pressure is sufficient to overcome the pressure of the spring means. When the poppet is displaced from the seated position, flow is possible in either direction along the flow path, herein defined as the "pass" position.

The term "pusher" means a specific type of rigid movable member used in the preferred embodiments of the invention described hereinafter.

The expression "orientation of the poppet relative to the seat" is intended to indicate the various orientations or attitudes of the poppet head relative to the associated seat which are dependent upon the movement of the movable member or pusher. Thus "orientation" includes the situation where (i) the pusher is relaxed, the poppet remains seated and the flow path is sealed; (ii) the pusher is moved so that the wall of the housing adjacent the poppet is displaced inwardly, the poppet is moved relative to its seat and the flow path is unsealed; and (iii) the pusher is moved against the side or edge of the seat so that the flow path around the seat and the head of the poppet is distorted thereby allowing flow around the poppet without actually moving the poppet.

The term "step" means that part of the stepped profile in the distal wall of the indented portion about which the poppet can pivot to facilitate displacement in the "pass" position.

A valve according to the invention comprises two elements as described above juxtaposed in series with the poppet heads facing opposite directions. When the movable members are arranged to move the poppets to achieve orientation (ii) as described above the poppets may be mounted either so that the heads face each other (head-to-head) or face away from each other (end-to-end). In a preferred embodiment the poppets are mounted head-to-head. When the movable members are arranged for orientation (iii) the end-to-end mounting is preferred because the distortion of the flow path around one of the poppet heads would make it difficult to maintain a complete seal (when desired) around the other poppet head, unless special precautions (such as an extra large separation) are taken.

Thus, according to the invention there is also a provided a valve for controlling flow of fluid through a flow path, which valve comprises a housing defining said flow path and having two indented portions about said flow path, a poppet mounted within each of said indented portions such that the internal end of each indented portion defines a seat which provides a fluid tight seal when the associated poppet head is held against said seat, spring means associated with each poppet for holding each poppet against each seat, a rigid movable means associated with each poppet for altering the orientation of the associated poppet relative to its seat and thereby seal or unseal the flow path around said poppet, and actuating means for moving each movable means.

Preferably, the movable members are adapted, when moved by the actuating means, to move the poppets relative to the seats and the poppets are mounted in series in head-to-head juxtaposition.

In such a preferred embodiment, preferably the distal wall of each indented portion includes a step about which the poppet can pivot when moved by the movable member.

The invention further provides a valve system comprising two valves as described above mounted in series with each other.

The invention still further comprises a valve system comprising two valves as described above mounted in parallel with each other.

In the above described alternative embodiments, when the valves are in series with each other it is preferred that the movable members or pushers are located on one side of the housing; and when the valves are mounted in parallel, the movable members associated with each valve, or pair of elements, preferably are mounted on opposite side of the housing. The embodiments will be more particularly describe hereinafter.

In each of the above embodiments the actuating means is preferably a rigid slider having guiding grooves which, respectively, allow the movable member to be in the relaxed or "up" position or push the movable member against the wall of the housing (the "down") position.

A preferred embodiment of the invention is an apparatus which incorporates a valve or valve system as described above, which apparatus comprises a reservoir for liquid, a conduit for conveying liquid from and to said reservoir through said valve or valve system and through a connector for delivering said liquid to a device to be inflated, means for moving liquid to and from the inflatable device and a pressure indicator including a plunger for preventing over pressurization by said liquid.

In preferred embodiments of the apparatus, the means for moving liquid is preferably a trigger operated piston pump, a squeezable bulb pump or a syringe. Preferably, each of the said pump or syringe means is adapted to be operated by a single hand.

BRIEF DESCRIPTION OF THE DRAWINGS

Preferred embodiments of the invention are illustrated in the accompanying drawings, in which.

DETAILED DESCRIPTION OF THE INVENTION

The invention will be more particularly described with reference to the preferred embodiments illustrated in the accompanying drawings.

Figure 1:
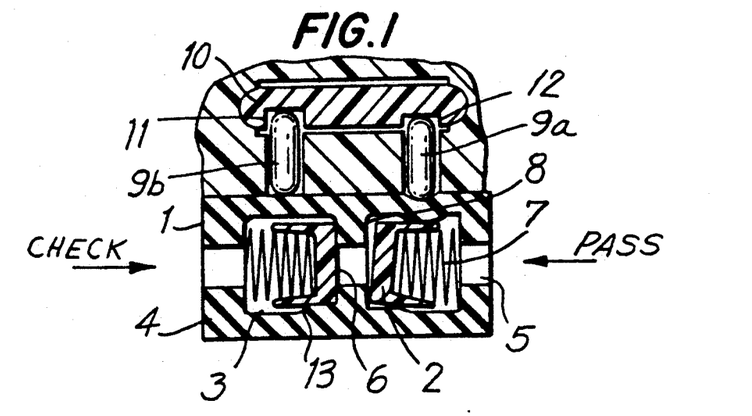
FIG. 1 is a section through a valve comprising two elements according to the invention in series with the poppets in the head-to-head mounting.

FIG. 1 illustrates, in section, a valve 1 comprising two elements in series. Each element has a poppet 2 mounted within an indented portion 3 of a housing 4 which defines a flow path 5 for fluid. The housing is made from a resilient material which has a memory so that the wall of the housing is adapted to be displaced inwardly in a desired manner when an appropriate force is applied to the outer surface and the wall returns to its original configuration when said force is withdrawn. Examples of suitable resilient materials are elastomers such as rubber, silicone rubber or other synthetic rubbers.

Each poppet 2 is substantially cup-shaped with a flat forward head 6. The inside of the cup accommodates a spring 7 which pushes the poppet head against a seat 8 defined by the internal end of the indented portion of the housing which holds the relevant poppet. The spring is preferably made of a corrosion-resistant metal such as stainless steel.

The poppet cup is preferably made from a corrosion-resistant rigid material such as a plastic, for example, an acetal resin, such as that available under the trade name Delrin, or a metal, for example, stainless steel. The force to displace the wall of the housing is applied by a rigid movable member 9, hereafter referred to as a "pusher". Each pusher is moved up or down by actuating means in the form of a rigid slider 10 having guiding grooves 11, 12 which are deep or shallow so as, respectively, to allow the pusher to be in the up position, i.e. relaxed, or to push the pusher to the down position. When a deep groove 11 of the slider is in contact with the upper end of a pusher the resilience of the housing wall touching the lower end of the pusher will keep the pusher 9b in the up position, the wall of the housing will not be displaced, the poppet remains seated and the flow path is sealed in the back-to-front direction. When the slider is moved so that a shallow groove 12 contacts the upper end of a pusher, the pusher 9a is pushed down so that the lower end thereof displaces the wall of the housing thereby unseating the poppet as shown with respect to the right poppet in FIG. 1 and the left poppet in FIG. 2. To facilitate unsealing of the flow path, the distal wall of the indented portion 3 has a step 13 about which the poppet 2 can pivot when it is moved by the pusher 9a.

Thus, if the groove configuration (deep 11) allows both pushers to remain in the up position the poppets 2 remain seated and the valve checks flow in both directions. If the groove configuration (shallow 12) pushes both pushers down 9a the poppets are unseated and the valve allows fluid to pass in both directions. If the slider is moved so that the right pusher 9a is down and the left pusher 9b is up (FIG. 1) the right poppet is unseated and fluid under pressure can pass from right to left but is checked from left to right.

In another slider position (FIG. 2) the left pusher 9a is down and the right pusher 9b is up so that the left poppet is unseated and the pass and check directions are opposite to those applicable to the embodiment shown in FIG. 1.

Figure 2:
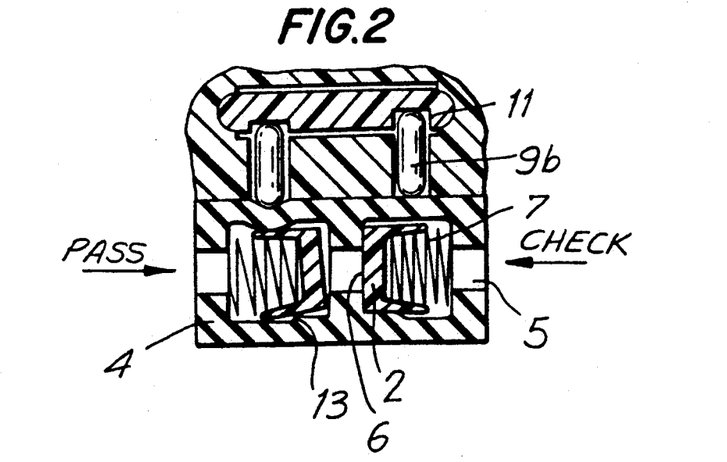
FIG. 2 illustrates the same valve as in FIG. 1 but with the poppets in different orientations.

Both FIG. 1 and FIG. 2 illustrate an embodiment wherein the valve comprises two elements in series with the poppets mounted head-to-head and the change in orientation of the poppets to obtain the pass position is achieved by displacement of the poppet head 6 relative to the seat 8.

Figure 3:
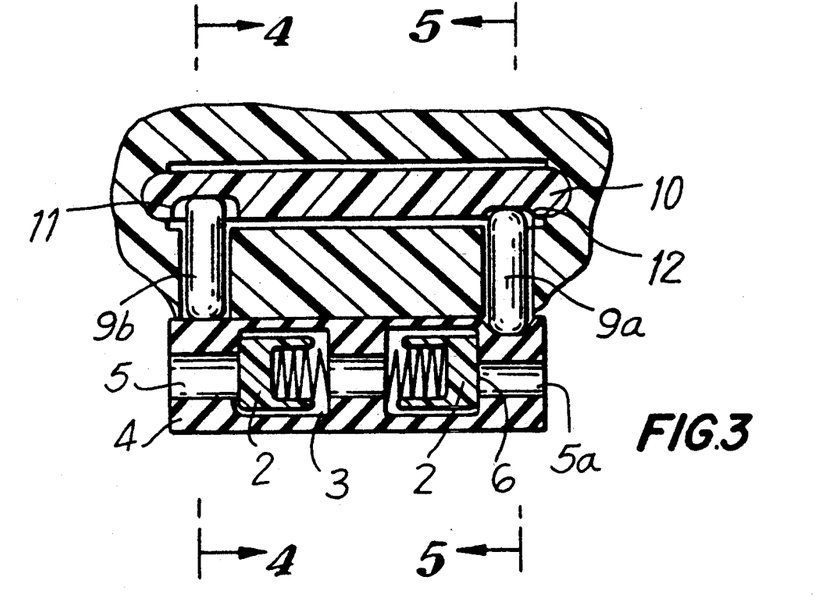
FIG. 3 is a section through a valve comprising two elements in series with the poppets in end-to-end mounting and the movable members arranged to be adapted to distort the flow path around the poppet heads.

FIG. 3 illustrates an alternative embodiment wherein the elements are also in series but the poppets are mounted end-to-end and the pass position is achieved by distortion of the flow path around the head of the poppet.

Figure 4:
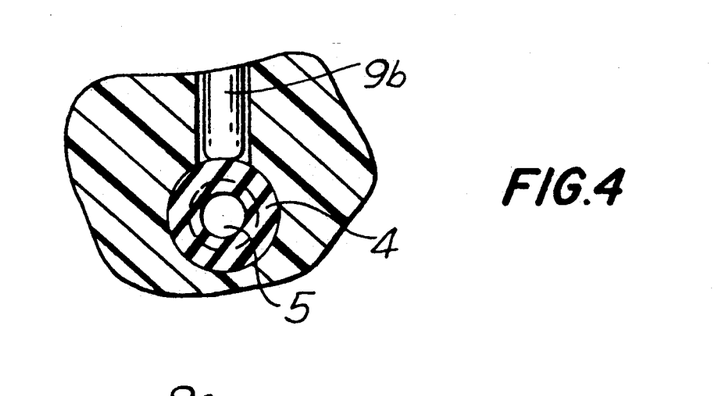
FIG. 4 is a partial section through line 4—4 of FIG. 3.
Figure 5:
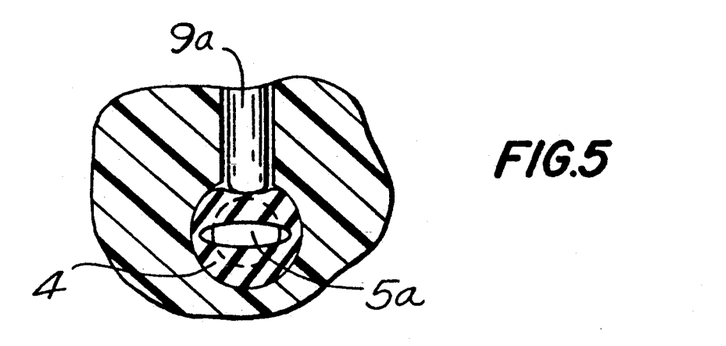
FIG. 5 is a partial section through line 5—5 of FIG. 3.

In the embodiment illustrated in FIG. 3 the portion of the flow path 5a beneath the downwardly pushed pusher 9a is flattened so that the substantially circular cross-section of the undistorted flow path 5 (see FIG. 4) assumes a flattened oval shape 5a as shown in FIG. 5, allowing fluid flow around the vertical sides of the poppet head. Since the poppet itself is not physically displaced in this embodiment, the step in the distal wall of the indented portion is not necessary for the pivotal movement. However, the step may be retained, if desired, to keep the poppet head centrally disposed in the flow path.

Figure 6:
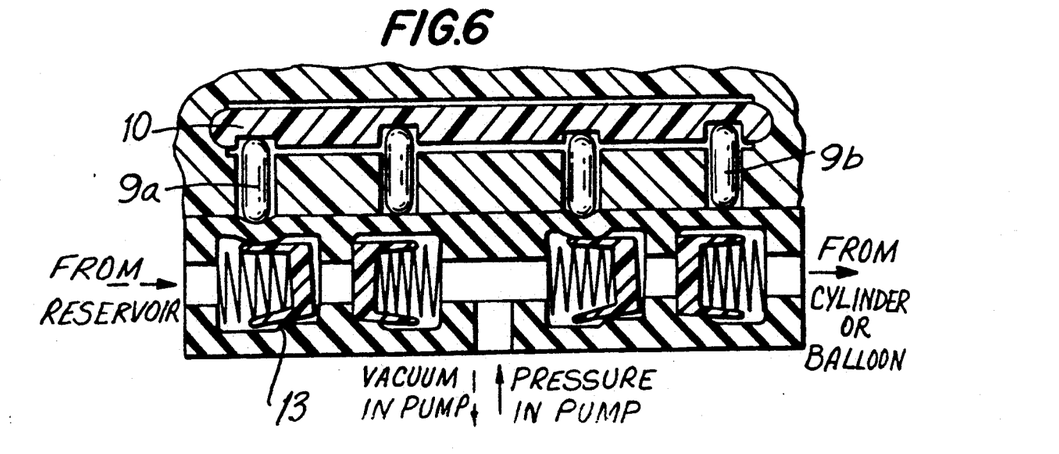
FIGS. 6 and 7 illustrate different poppet orientations of an embodiment comprising two valves in series.
Figure 7:
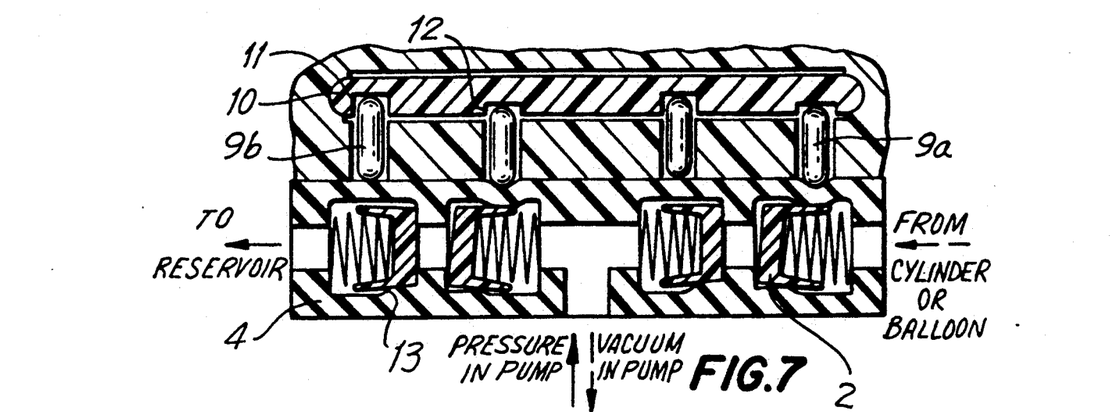
Figure 8:
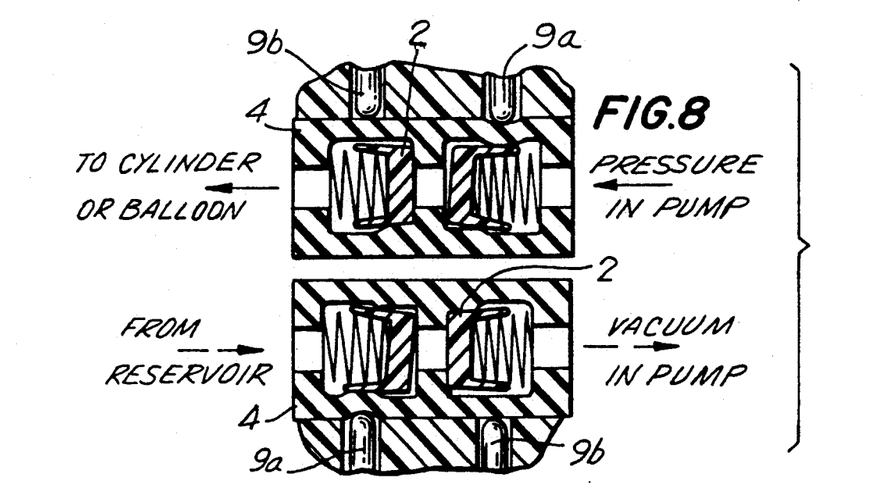
FIG. 8 and FIG. 9 illustrate different poppet orientations of an embodiment comprising two valves in parallel.
Figure 9:
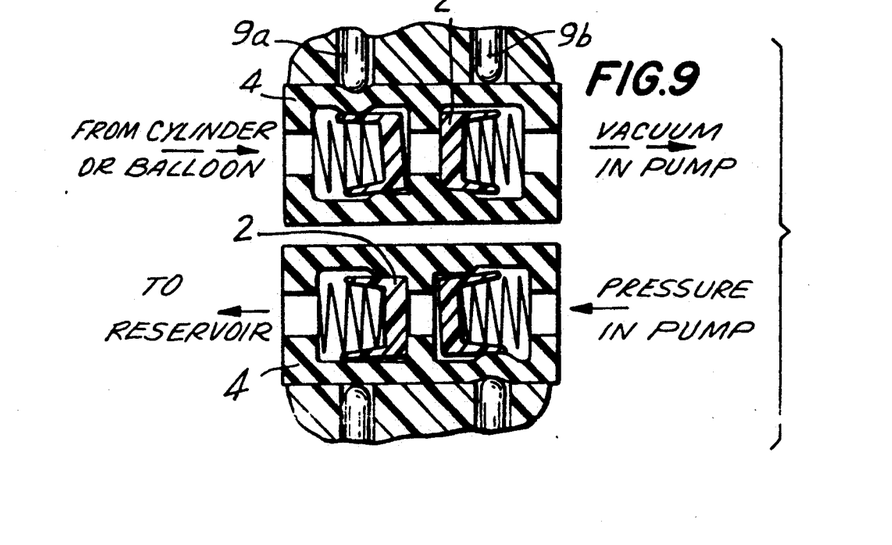

Two valves may be assembled in series as illustrated in FIG. 6 and FIG. 7 or in parallel or illustrated in FIG. 8 and FIG. 9.

The valves or valve assembly according to the invention may have many different applications.

One application is to control the direction of fluid flow in a device such as an inflator for a balloon dilator (FIGS. 10-13), a pump for an inflatable penile prosthesis (FIG. 14 and FIG. 15), or a high pressure syringe for an angioplasty balloon catheter (FIGS. 16-19).

Each of the above devices is shown with valves in parallel assembly.

Figures 10, 11:
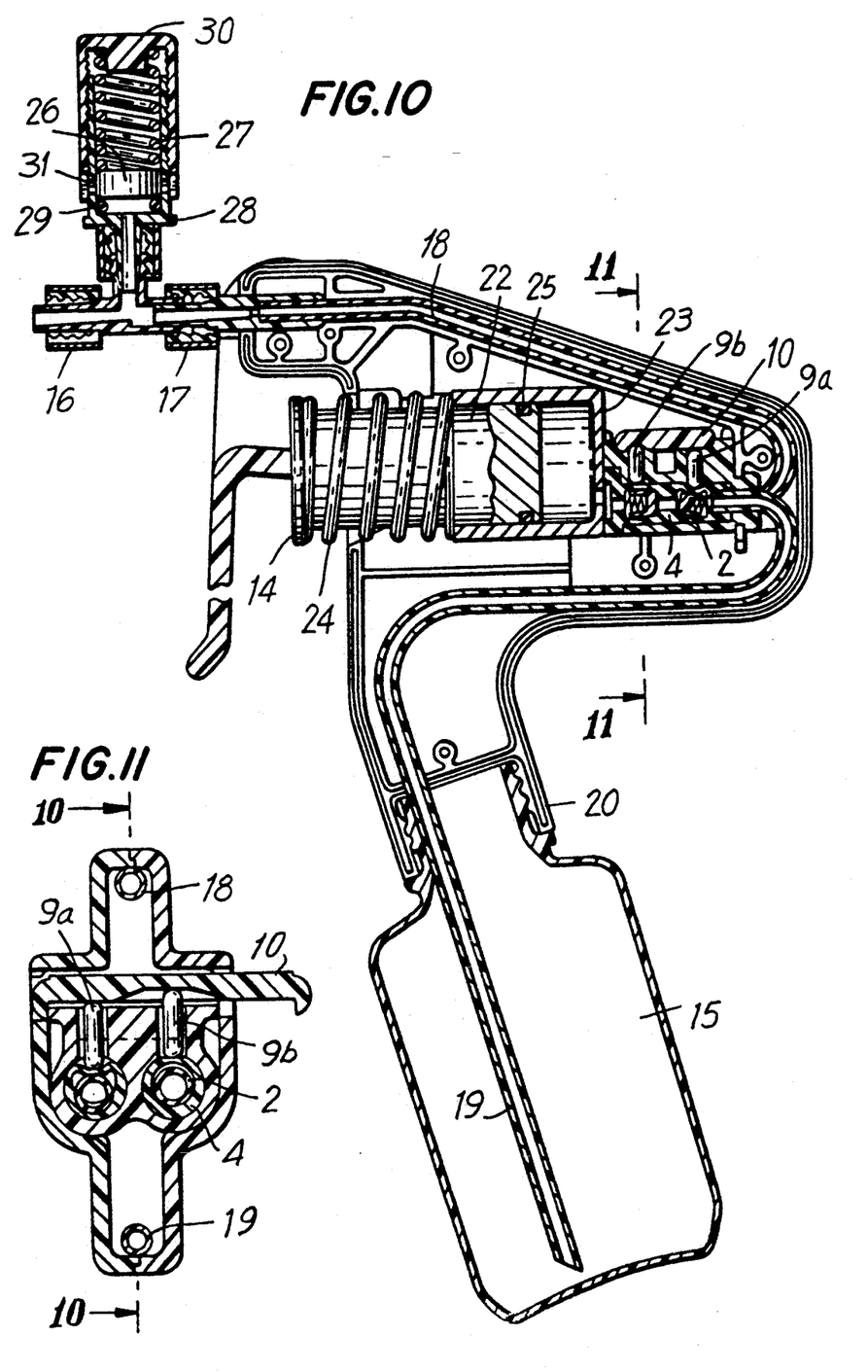
FIG. 10 is a side elevation of an apparatus incorporating a valve according to the invention.
FIG. 11 is cross-section through the valve-containing portion along line 11—11 of the apparatus of FIG. 10.

In the inflator illustrated in FIG. 10, when the slider 10 is in the position shown the rear pusher 9a is down and the associated poppet is unseated. In this position, when the piston pump 14 is operated, liquid from a reservoir 15 flows to a catheter with a dilation balloon (not shown) and inflates the balloon. The catheter is connected to the inflator through two luer locks 16, 17. When the slider 10 is moved to the opposite position from that shown, upon operation of the pump, the inflator deflates the balloon by transferring liquid from the balloon to the reservoir 15 through flexible high pressure tubing 18, 19. The position of the slider 10 and the relevant orientation of the two forward pushers and poppets is shown in FIG. 11.

The removable reservoir 15 may be re-usable or disposable and is attached to the inflator housing 20 through a screw fitting. The reservoir is preferably made from a sterilizable rigid plastic, such as Delrin, Ultem, a polycarbonate or a polysulfone.

The operation mode of the inflator is the same for balloon inflation and deflation. Thus, a trigger 21 is squeezed and released to achieve a reciprocating motion of a piston 22 within a pump chamber defined by a sleeve 23. The pump piston operates against a compression spring 24 and pressure is built up within the pump chamber with the aid of an O-ring seal 25 between the piston 22 and the sleeve 23. The seal may be made from natural or synthetic rubber or any suitable elastomer. In a preferred embodiment, for ease of assembly and disassembly for replacement, the seal may have a U-shaped cross-section. A plunger-type pressure indicator measures pressure in the dilation balloon to ensure that the balloon is not over-dilated. The pressure indicator comprises a plunger 26 loaded with a calibrated compression spring 27 within a housing 28. A seal 29 between the plunger and the housing prevents leakage of liquid. Compression of the spring may be adjusted by a screw-type cap 30.

By repeating the trigger 21 squeezing-releasing operation an operator can pressurize a balloon to a predetermined pressure. The pressure indicator shows the balloon pressure. If the operator continues to squeeze the trigger 21 after the predetermined pressure is reached liquid will be expelled through a slot 31, when the plunger reaches the slot and this prevents excess pressurization of the balloon.

Figures 12, 13:
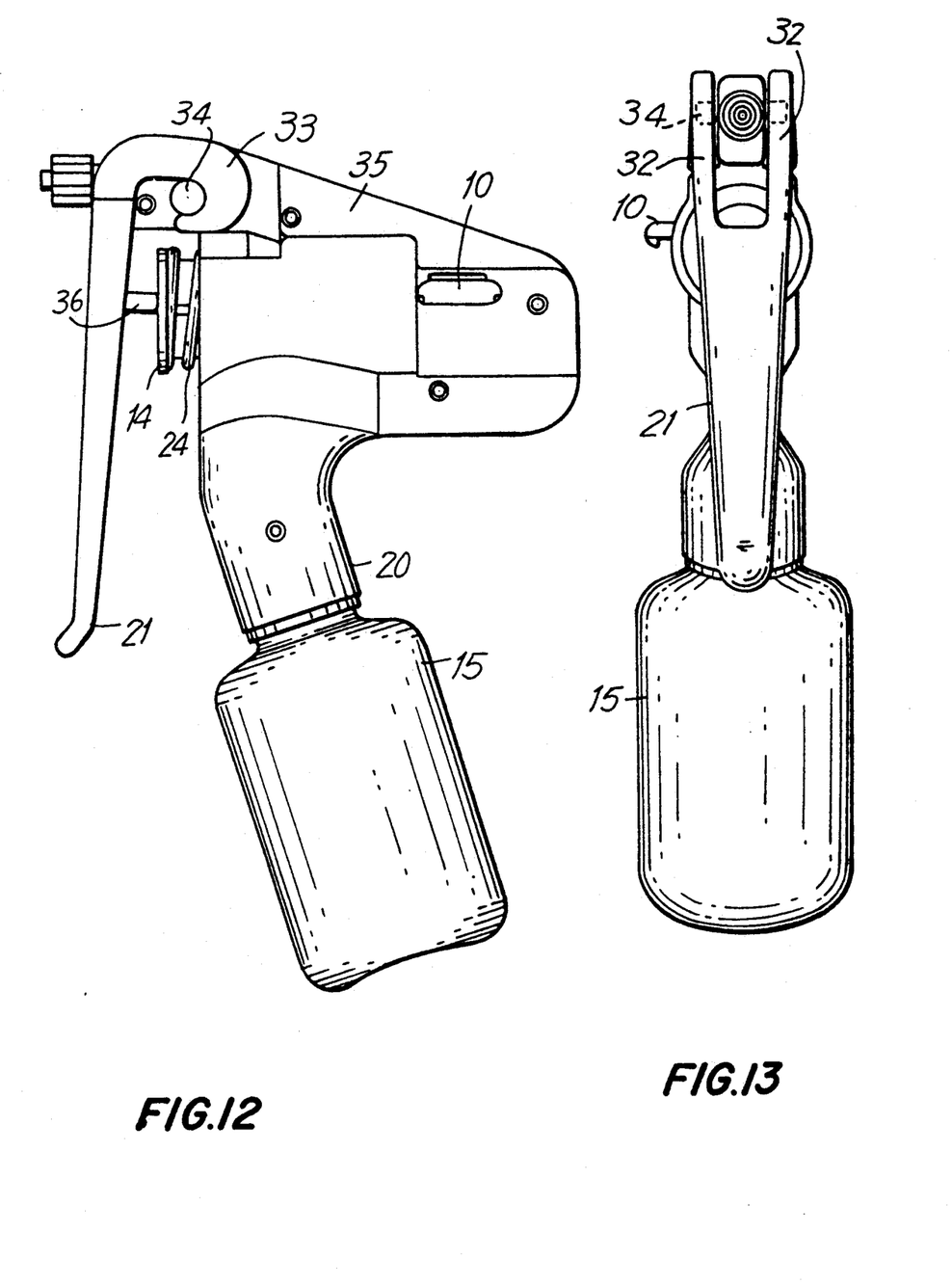
FIG. 12 is a side elevation of an inflator with a removable trigger.
FIG. 13 is an end elevation of the inflator of FIG. 12.

FIG. 12 is a side elevation of an embodiment with a removable trigger 21. The upper end of the trigger is bifurcated and each prong 32 of the fork terminates in a hook 33 which pivots about a fulcrum 34 formed by protruding circular flanges (shown by dotted lines in FIG. 13) on the sides of the body 35 of the inflator.

The trigger has a protruding member 36 which bears against the end of the piston 14. To remove the trigger the piston is depressed against spring 24 by hand and the hook 33 may then be slid over the fulcrum 34. The trigger may be removed for ease of sterilization or disinfection, or for maintenance, i.e. replacement of the seal 25 (see FIG. 10) or of any other part, such as the piston, spring or the trigger itself. The trigger is preferably made from a high strength rigid plastic, such as Ultem.

Figure 14:
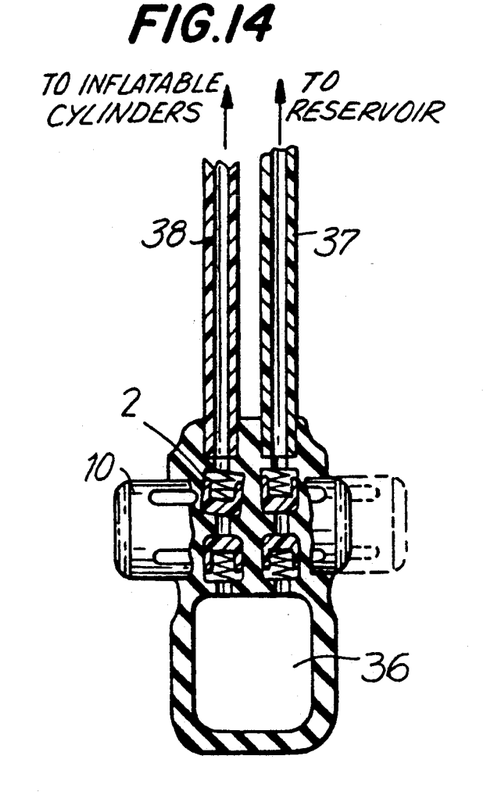
FIG. 14 is a section through another embodiment of the invention.
Figure 15:
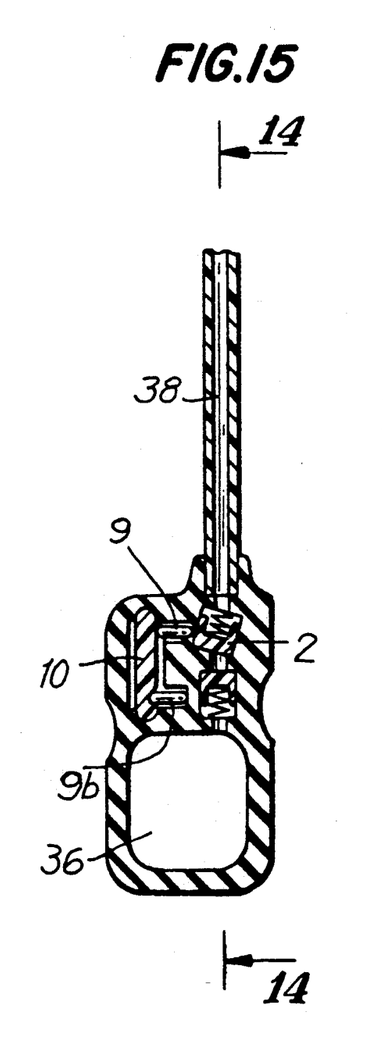
FIG. 15 is a cross-section through the valve-containing portion of the embodiment of FIG. 14.

FIG. 14 and FIG. 15 illustrate a bulb pump for an inflatable penile prosthesis, which pump has a parallel valve assembly similar to that illustrated in FIGS. 8-10. The pump operates by squeezing and releasing the bulb 36 to inflate the cylinder or cylinders (not shown) of a penile prosthesis with liquid from a reservoir (not shown). When the poppets 2 are in the pass position from reservoir to cylinder, liquid under pressure is moved by the pump along a tube 37 from the reservoir through the valve assembly and then through a tube 38 to the cylinder. When the slider 10 is moved by an operator to the opposite position operation of the pump results in deflation of the cylinders by movement of liquid under pressure from the cylinder or cylinders to the reservoir via the valve assembly and the pump bulb 36.

To achieve a desired flaccidity an operator may pump out substantially all the liquid from the cylinder or cylinders to the reservoir. The valve assembly also provides a complete "lock out" effect under any pressure in the reservoir, preventing a spontaneous inflation of the cylinders. The illustrated pump and valve assembly arrangement allows a pressurizable reservoir to be used and therefore reduces the number of pump bulb squeezes required for a proper cylinder inflation.

FIGS. 16-19 illustrate a syringe-type inflator for an angioplasty balloon catheter. This embodiment is adapted to provide much higher liquid pressure than the embodiment of FIG. 10; for example, up to 300 p.s.i. or about 20 atmospheres, compared to about 60 p.s.i. or 4 atmospheres for the inflator of FIG. 10; in combination with a lower displacement volume.

Figure 16:
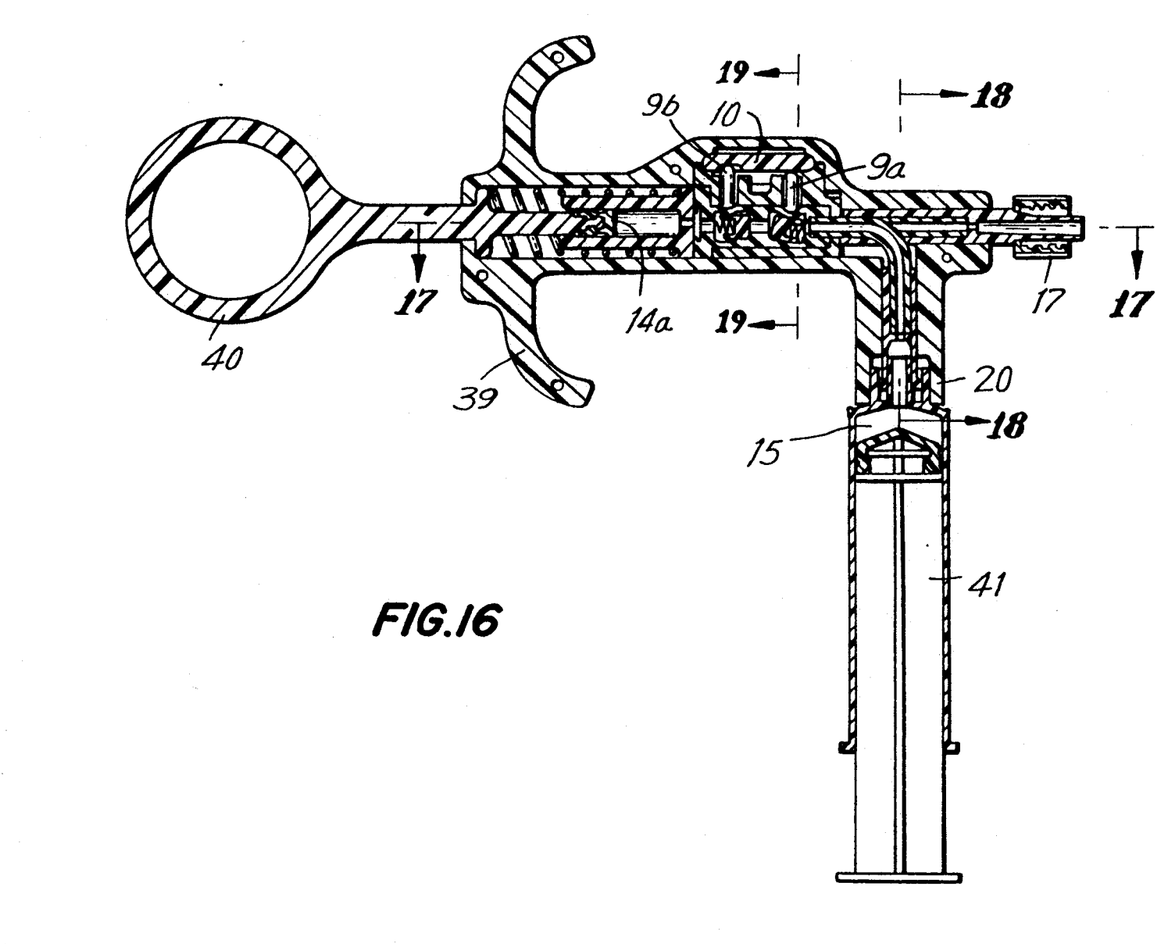
FIG. 16 is a side elevation, partly in section, of a high pressure syringe for an angioplasty balloon catheter.
Figure 17:
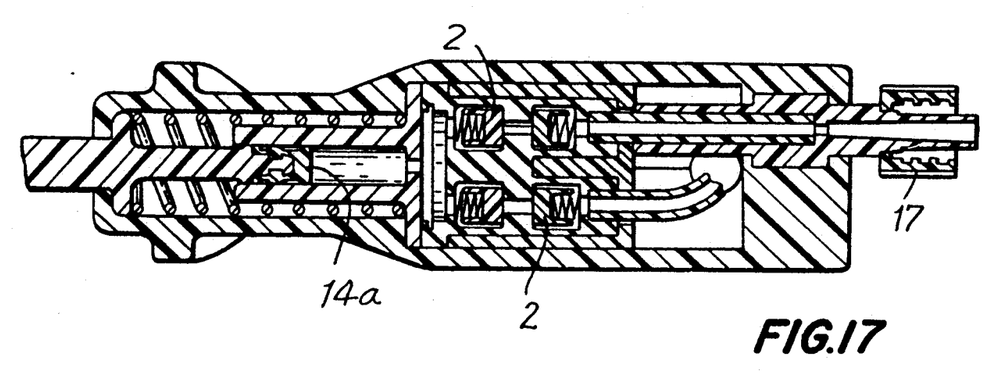
FIG. 17 is a section through line 17—17 of FIG. 16.
Figure 18:
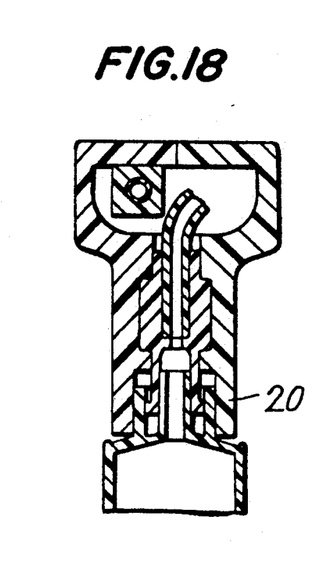
FIG. 18 is a vertical section through line 18—18 of FIG. 16.
Figure 19:
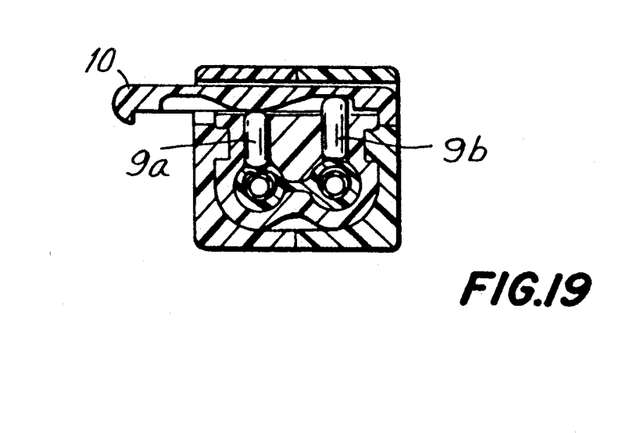
FIG. 19 is a section through line 19—19, i.e. through the slider and pusher mechanism of the embodiment of FIG. 16.

The valve operation is substantially the same as that in the inflator described above, but in this embodiment the pressure to move the liquid from the syringe-type reservoir 15 is provided by a plunger 14a adapted to be actuated by a handle 39,40 operated by two fingers and thumb of a single hand. The volume of liquid in the reservoir 15 may be adjusted by movement of a plug 41.

The embodiments illustrated herein provide easier and faster operation of the relevant devices, for example single-handed operation, automatic safety features and re-usability. Thus, they may be sterilized or disinfected when required.

I claim:

1. An element of a valve for controlling flow of a fluid through a flow path, which element comprises a housing defining said flow path and having an indented portion about said flow path, a poppet mounted within said indented portion such that an internal end of the indented portion defines a seat which provides a fluid-tight seal when the poppet mounted within the indented portion is held against said seat, spring means for holding said poppet against said seat, rigid movable means associated with the poppet. For altering the orientation of said poppet relative to said seat and thereby seal or unseal the flow path, and actuating means for moving said movable means.

2. An element according to claim 1, in which orientation of the poppet relative to its seat is altered by moving the rigid movable means to displace the wall of the housing adjacent the poppet and thereby move the poppet relative to its seat.

3. An element according to claim 2, in which the distal wall of the indented portion has a step about which the poppet can pivot when it is moved by the movable means.

4. A valve for controlling flow of fluid through a flow path, which valve comprises a housing defining said flow path and having two indented portions about said flow path, a poppet mounted within each of said indented portions such that the internal end of each indented portion defines a seat which provides a fluid tight seal when the associated poppet head is held against said seat, spring means associated with each poppet for holding each poppet against each seat, rigid movable means associated with each poppet for altering the orientation of the associated poppet relative to its seat and thereby seal or unseal the flow path around said poppet, and actuating means for moving each movable means.

5. A valve according to claim 4, in which the movable means, when moved by the actuating means, are adapted to move the poppets relative to the seats and the poppets are mounted in head-to-head juxtaposition.

6. A valve according to claim 5, in which the distal wall of each indented portion includes a step about which the poppet can pivot when moved by the movable means.

7. A valve system comprising two valves according to claim 4 mounted in series with each other.

8. A valve system comprising two valves according to claim 4 mounted in parallel with each other.

9. An apparatus for conveying fluid to or from an inflatable device which apparatus comprises a reservoir for said fluid, a flow path defined by conduit means from said reservoir and terminating in connecting means for connecting said apparatus to said inflatable device, pump means for pumping fluid through said flow path and valve means for controlling the flow of fluid which valve means comprises at least one valve according to claim 4.

10. An apparatus according to claim 9, in which said pump means comprises a trigger-operated piston pump and said apparatus is an inflator for a balloon dilator.

11. An apparatus according to claim 10, in which the trigger of said trigger-operated pump is removable.

12. An apparatus according to claim 9, in which said pump means is a bulb pump and said apparatus is an inflator for an inflatable penile prosthesis.

13. An apparatus according to claim 9, in which said pump means is a high-pressure syringe and said apparatus is an inflator for an angioplasty balloon catheter.

* * * * *